(12) United States Patent  
Tomoto

(10) Patent No.: US 8,666,135 B2  
(45) Date of Patent: Mar. 4, 2014

(54) IMAGE PROCESSING APPARATUS

(71) Applicant: Olympus Medical Systems Corp., Tokyo (JP)

(72) Inventor: Yusuke Tomoto, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/748,970

(22) Filed: Jan. 24, 2013

(65) Prior Publication Data

US 2013/0208958 A1 Aug. 15, 2013

Related U.S. Application Data

(63) Continuation of application No. PCT/JP2012/062381, filed on May 15, 2012.

(30) Foreign Application Priority Data

Jul. 12, 2011 (JP) .................... 2011-154215

(51) Int. Cl.  
*G06K 9/00* (2006.01)

(52) U.S. Cl.  
USPC ........................................ 382/128

(58) Field of Classification Search  
None  
See application file for complete search history.

(56) References Cited

U.S. PATENT DOCUMENTS

2011/0085717 A1    4/2011    Matsuda

FOREIGN PATENT DOCUMENTS

| EP | 2 305 091 A1 | 4/2011 |
|---|---|---|
| JP | 02-124131 | 5/1990 |
| JP | 2005-034211 | 2/2005 |
| JP | 2006-141734 | 6/2006 |
| JP | 2006-239270 | 9/2006 |
| JP | 2009-297450 | 12/2009 |
| JP | 2010-184057 | 8/2010 |
| WO | WO 2009/154125 A1 | 12/2009 |

*Primary Examiner* — Stephen R Koziol  
*Assistant Examiner* — Raphael Schwartz  
(74) *Attorney, Agent, or Firm* — Scully, Scott, Murphy & Presser, P.C.

(57) ABSTRACT

An image processing apparatus includes: an image input section via which a medical image picked up of a mucous surface of a living body is inputted; a setting section that sets a region of interest as a first region and a second region including a unit region in the medical image; a feature value calculating section that calculates a first feature value relating to a shape of the region of interest based on pixel values of the region of interest and a region in a periphery thereof and a second feature value relating to a shape of the unit region based on pixel values of the unit region and a region in a periphery thereof; and an matching section that matches the region of interest with a predetermined shape based on distributions of the first feature value and the second feature value calculated by the feature value calculating section.

3 Claims, 16 Drawing Sheets

FIG.4
(A)
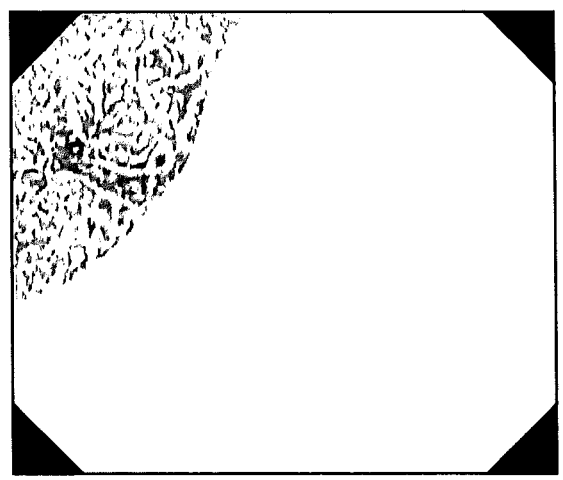
(B)
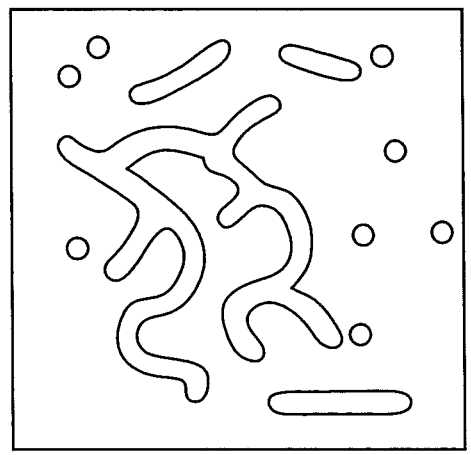

| PIXEL | FEATURE VALUES |
|---|---|
| PIXEL (1, 1) | · · · · |
| PIXEL (1, 2) | · · · · |
| · · · · | · · · |
| PIXEL (n, n) | · · · · |

FIG.7
(A)
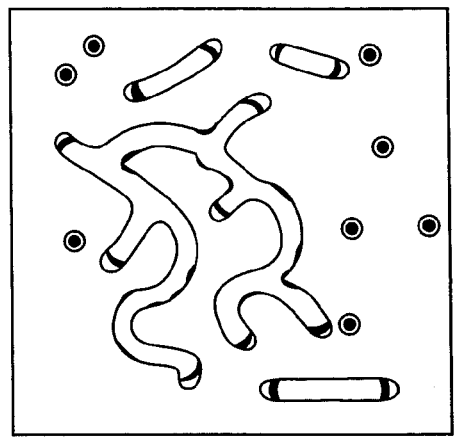
● CIRCLE
○ LINE
(B)
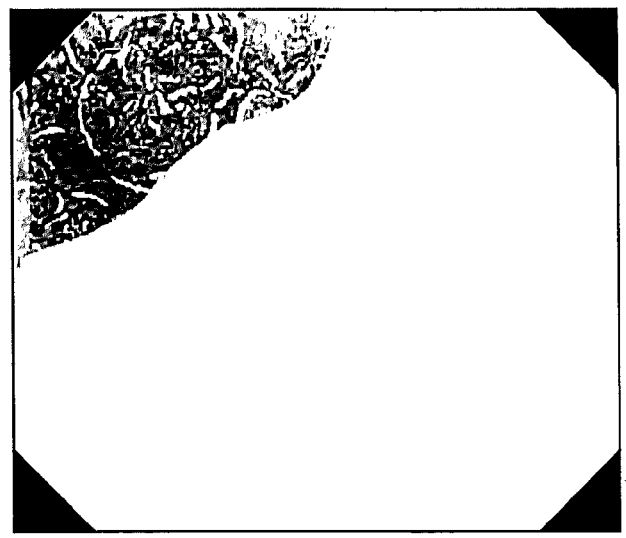

FIG.8
(A)
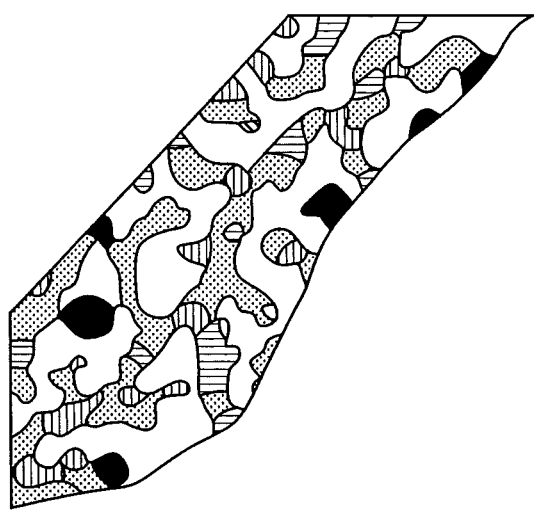
⊖ STRAIGHT LINE
● CIRCLE
⊙ CURVE
⑪ DIVARICATION
(B)
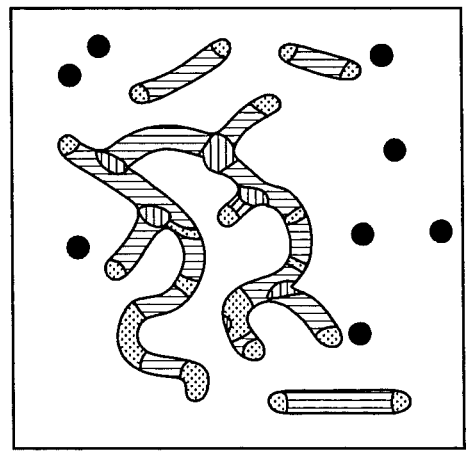

FIG.14
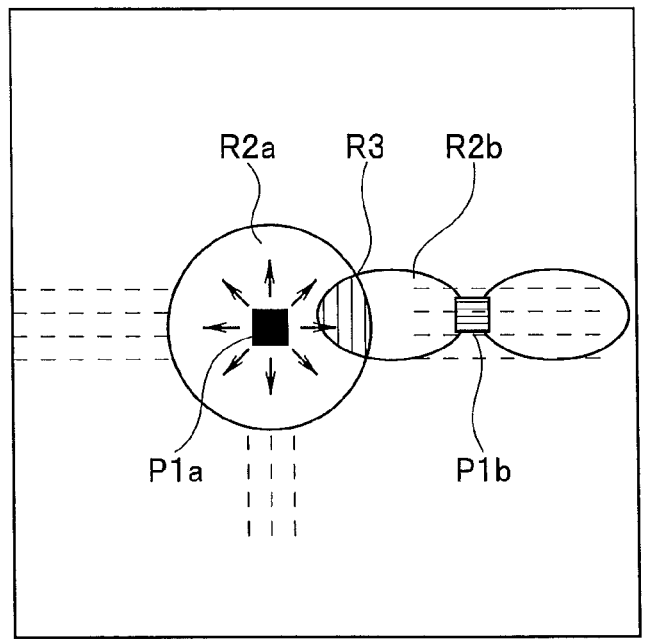
FIG.15
(A) 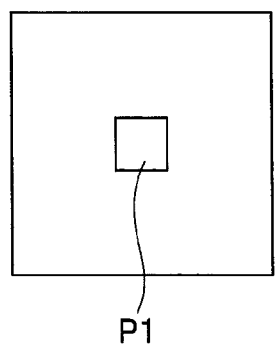
(B) 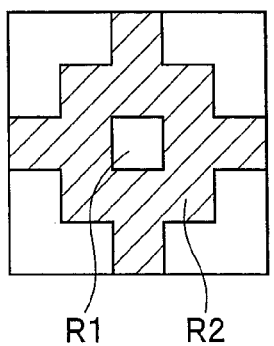
(C) 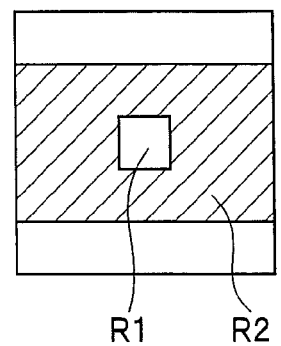

FIG.20
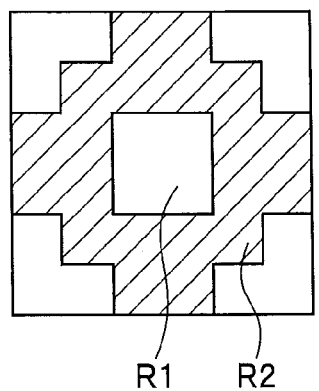
(A)
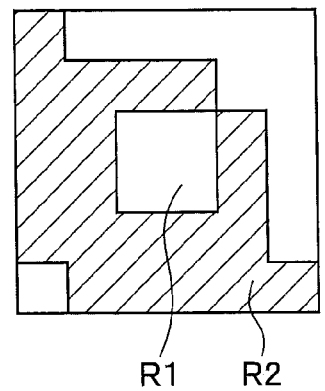
(B)

IMAGE PROCESSING APPARATUS

CROSS REFERENCE TO RELATED APPLICATION

This application is a continuation application of PCT/JP2012/062381 filed on May 15, 2012 and claims benefit of Japanese Application No. 2011-154215 filed in Japan on Jul. 12, 2011, the entire contents of which are incorporated herein by this reference.

BACKGROUND OF THE INVENTION

1. Field of the Invention

The present invention relates to an image processing apparatus that performs image processing of a medical image so that the image can easily be used for, e.g., diagnosis.

2. Description of the Related Art

In recent years, in a medical field, endoscopes have come to be widely used for performing, e.g., examinations and/or diagnosis.

Also, methods for performing image processing of a medical image picked up via an endoscope by inserting the endoscope into a lumen inside a patient's body, using patterns of microstructures of submucosal vessels and/or mucous surfaces by means of a computer-used diagnosis support system so that surgeons can more easily and effectively use the image for, e.g., diagnosis.

In this case, it is necessary to quantify the patterns.

For example, Japanese Patent Application Laid-Open Publication No. 2005-34211, which is a first conventional example, discloses the following content: a partial image of interest is extracted from image data, and which density distribution pattern, from among density distribution patterns stored in density distribution pattern storing means, each pixel in a unit pixel group in the extracted partial image of interest is similar to is determined, and appearance frequency counts of the respective density distribution patterns appearing in the partial image of interest are done for the respective density distribution patterns to figure out a pattern histogram.

Then, the pattern histogram is repeatedly presented to learning means to make the learning means learn weights connecting an input node and an output node, and learned weight vectors connecting output nodes and respective input nodes, which have been learned, is obtained as a representing pattern histogram.

Japanese Patent Application Laid-Open Publication No. 2006-239270, which is a second conventional example, discloses the following content: a differential image between a first breast image, which is a diagnosis target, and a second breast image, which is a reference for determining a diseased region in the first breast image, is obtained, and a plurality of regions of interest ROI are set inside a lung-field region in the differential image.

Disease information indicating whether or not each of the regions of interest ROI has an interstitial lung disease is obtained to determine whether or not the lung-field region is a diseased region according to a frequency per unit area of the regions of interest ROI indicated as being an interstitial lung disease appearing in the lung-field region.

SUMMARY OF THE INVENTION

An image processing apparatus according to an aspect of the present invention includes: an image input section via which a medical image picked up of a mucous surface of a living body, the medical image including a plurality of pixels, is inputted; a setting section that sets a region of interest as a first region including one or more pixels in the medical image and sets a second region including a unit region including the one or more pixels that are different from those of the region of interest in the medical image; a feature value calculating section that calculates a first feature value relating to a shape of the region of interest based on a pixel value of the region of interest set by the setting section and a pixel value of a region in a periphery of the region of interest, and calculates a second feature value relating to a shape of the unit region based on a pixel value of the unit region and a pixel value of a region in a periphery of the unit region; and a matching section that matches the region of interest with a predetermined shape based on distributions of the first feature value and the second feature value calculated by the feature value calculating section.

BRIEF DESCRIPTION OF THE DRAWINGS

FIG. 4 includes diagrams illustrating a medical image inputted via an image input section;

FIG. 7 includes diagrams illustrating a structure region extracted from the image in FIG. 4;

FIG. 8 includes diagrams illustrating an image resulting from division based on respective basic shapes;

FIG. 14 is a diagram illustrating an operation where voting is employed for a divarication;

FIG. 15 includes diagrams illustrating examples of setting of second regions with shapes different from, e.g., that in FIG. 10;

FIG. 20 includes diagrams each illustrating an operation in FIG. 19.

DETAILED DESCRIPTION OF THE PREFERRED EMBODIMENTS

Embodiments of the present invention will be described below with reference to the drawings.

First Embodiment

Figure 1:
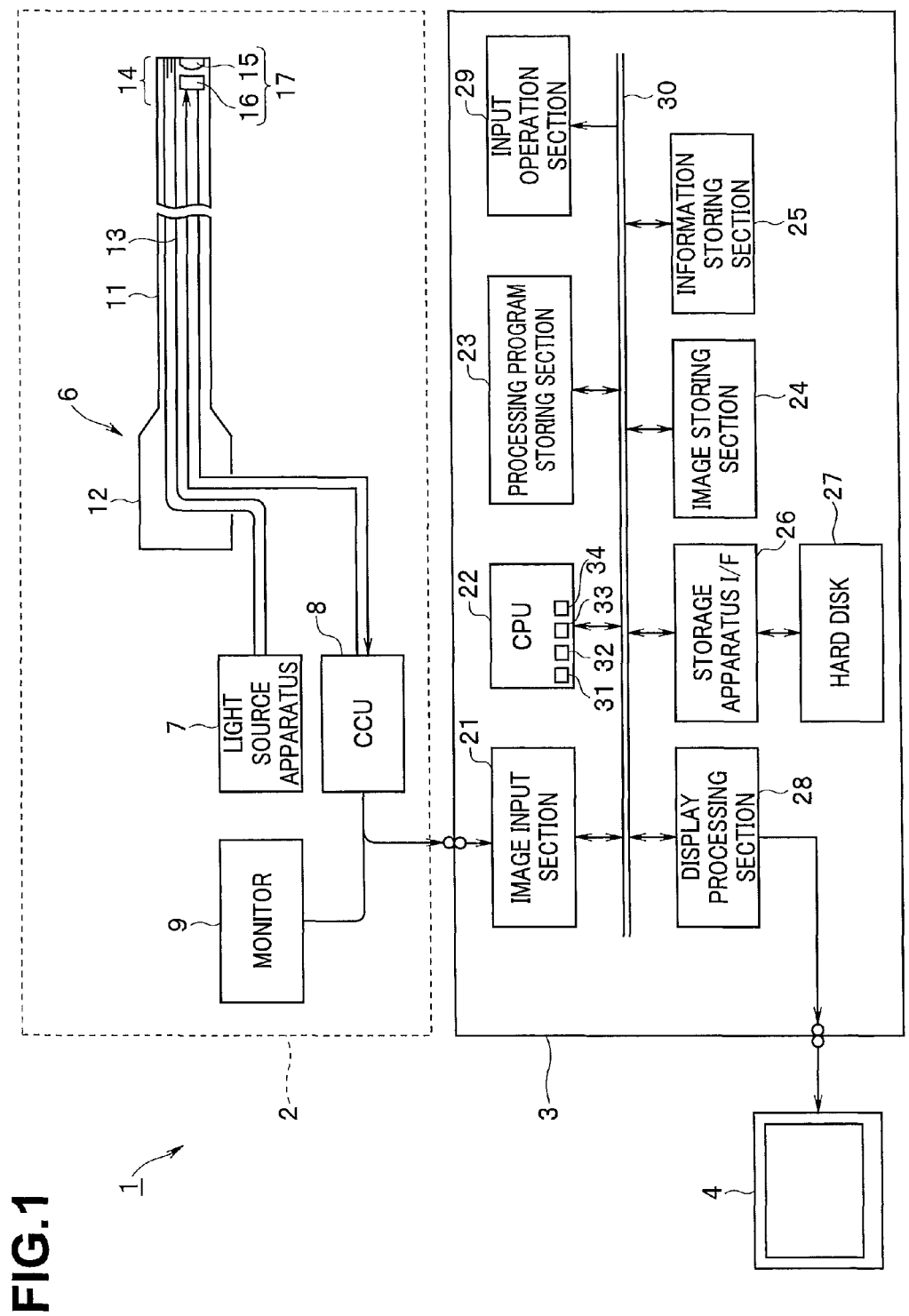
FIG. 1 is a diagram illustrating an overall configuration of an endoscope system including an image processing apparatus according to a first embodiment of the present invention.

An endoscope system 1, which is illustrated in FIG. 1, includes an endoscopic observation apparatus 2, an endoscopic image processing apparatus (hereinafter simply referred to as image processing apparatus) 3 according to the present embodiment, the image processing apparatus 3 including, e.g., a personal computer and performing image processing of an endoscopic image, which is a medical image obtained by the endoscopic observation apparatus 2, and a display monitor 4 that displays the image subjected to image processing by the image processing apparatus 3.

The endoscopic observation apparatus 2 includes an endoscope 6 to be inserted into a body cavity, a light source apparatus 7 that supplies illuminating light to the endoscope 6, a camera control unit (abbreviated as CCU) 8 that performs signal processing for image pickup means in the endoscope 6, and a monitor 9 that displays an endoscopic image taken via the image pickup device as a result of a video signal outputted from the CCU 8 being inputted thereto.

The endoscope 6 includes an insertion portion 11 to be inserted into a body cavity, and an operation portion 12 provided at a rear end of the insertion portion 11. Furthermore, a light guide 13 that conveys illuminating light is inserted inside the insertion portion 11.

A rear end of the light guide 13 is connected to the light source apparatus 7. Illuminating light supplied from the light source apparatus 7 is transmitted by the light guide 13 to make the (transmitted) illuminating light exit from a distal end face attached to an illumination window provided at a distal end portion 14 of the insertion portion 11 to illuminate an object such as a diseased part.

An image pickup apparatus 17 including an objective lens 15 attached to an observation window adjacent to the illumination window and, for example, a charge-coupled device (abbreviated as CCD) 16, which is a solid-state image pickup device arranged at an image forming position for the objective lens 15 is provided. An optical image formed on an image pickup surface of the CCD 16 is photoelectrically converted by the CCD 16.

The CCD 16 is connected to the CCU 8 via a signal wire, and upon application of a CCD drive signal from the CCU 8, the CCD 16 outputs the photoelectrically-converted image signal. The image signal is subjected to signal processing by a video processing circuit inside the CCU 8 and thereby converted to a video signal. The video signal is outputted to the monitor 9, and on a display surface of the monitor 9, an endoscopic image is displayed. The video signal is inputted also to the image processing apparatus 3.

The image processing apparatus 3 includes an image input section 21 via which a video signal corresponding to an endoscopic image (hereinafter simply abbreviated as image) inputted from the endoscopic observation apparatus 2 is inputted, a CPU 22, which is a central processing unit that performs image processing of image data inputted from the image input section 21, and a processing program storing section 23 that stores a processing program (control program) for making the CPU 22 perform image processing.

The image processing apparatus 3 also includes an image storing section 24 that stores, e.g., image data inputted from the image input section 21, an information storing section 25 that stores, e.g., information processed by the CPU 22, a hard disk 27, which is a storage apparatus that stores, e.g., the image data and the information processed by the CPU 22 via a storage apparatus interface 26, a display processing section 28 that performs display processing for displaying, e.g., the image data processed by the CPU 22, and an input operation section 29 including, e.g., a keyboard, via which a user performs an input of data, e.g., a parameter for image processing and/or an operation to provide an instruction.

A video signal generated by the display processing section 28 is displayed on the display monitor 4, and on a display surface of the display monitor 4, a processed image subjected to image processing is displayed.

Here, the image input section 21, the CPU 22, the processing program storing section 23, the image storing section 24, the information storing section 25, the storage apparatus interface 26, the display processing section 28 and the input operation section 29 are interconnected via a data bus 30.

Figure 2:
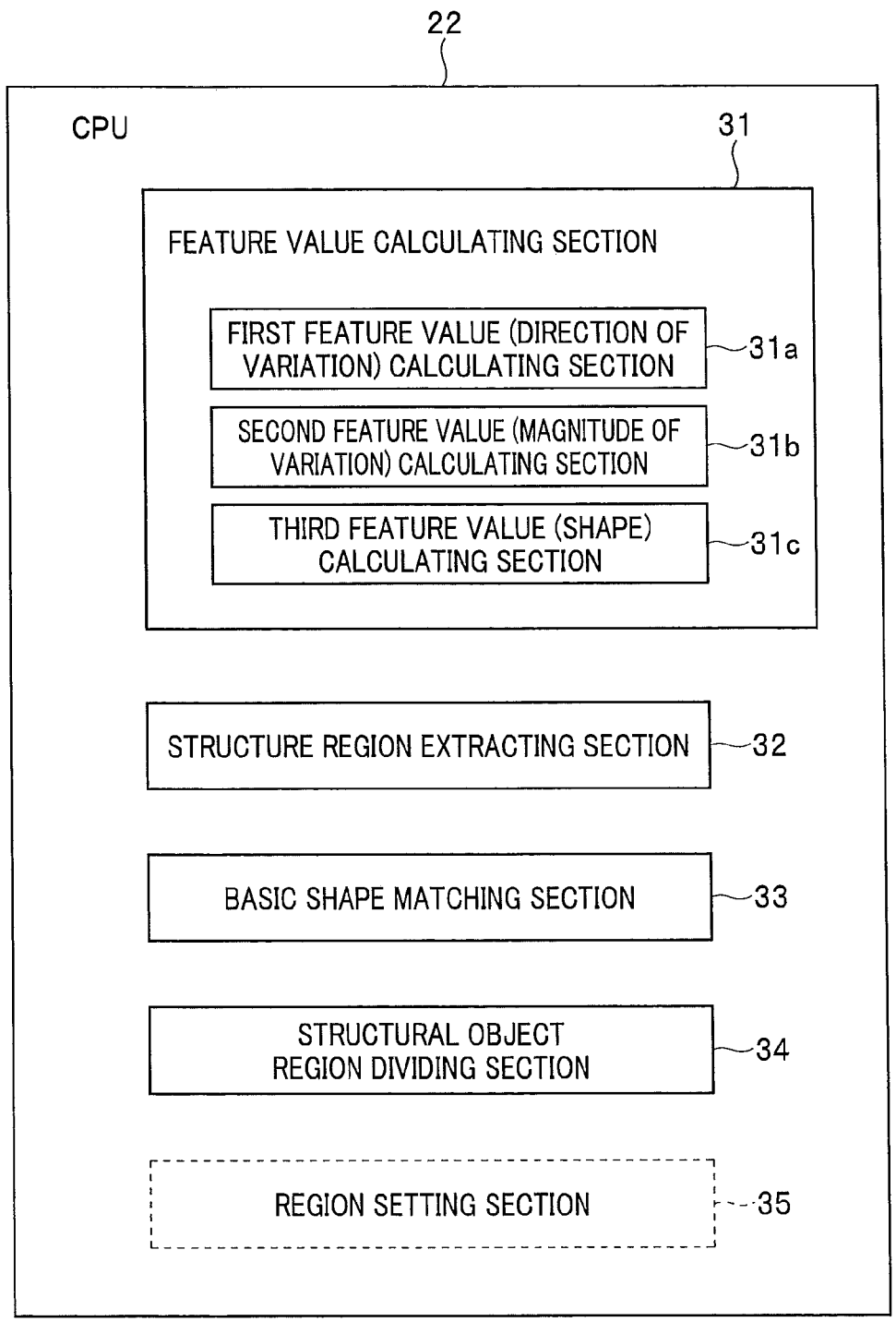
FIG. 2 is a block diagram illustrating processing functions such as a feature value calculating section included in a CPU.

FIG. 2 illustrates main processing functions included in the CPU 22 in the present embodiment. As illustrated in FIG. 2, the CPU 22 includes a processing function of a feature value calculating section 31 that calculates predetermined feature values of each pixel or each region in a medical image inputted from the image input section 21, and a processing function of a structure region extracting section 32 that extracts a desired structural object from the medical image as a structure region.

The feature value calculating section 31 includes a first feature value calculating section 31a that calculates a first feature value relating to a direction of local variation, a second feature value calculating section 31b that calculates a second feature value relating to a magnitude of local variation, and a third feature value calculating section 31c that calculates a third feature value relating to a local shape, from a pixel or a region to be processed as predetermined feature values.

The CPU 22 includes a processing function of a basic shape matching section 33 that matches each pixel or each region in the structure region with any of a plurality of predetermined basic shapes based on the feature values calculated by the feature value calculating section 31, and a processing function of a structural object region dividing section 34 that divides the structural object into regions according to the respective predetermined basic shapes based on results of matching by the basic shape matching section 33.

Note that as described in a second embodiment, which will be described later, the CPU 22 includes a processing function of a region setting section (or a region selecting section) 35 that selectively sets a first region including one or more first pixels and a second region including one or more pixels in a peripheral portion of the first region (indicated by dotted lines in FIG. 2). The present invention is not limited to a case where the CPU 22 is configured by including the feature value calculating section 31, the structure region extracting section 32, the basic shape matching section 33, the structural object region dividing section 34 and the region setting section 35, and, e.g., may be configured by including dedicated electronic circuits using hardware. Note that in the case of, e.g., a CPU 22 in FIG. 18, which will be described later, functions provided by the CPU 22 may be configured by, e.g., dedicated electronic circuits.

The image processing apparatus 3 according to the present embodiment, which has such configuration as described above, includes: the image input section 21, which is image input means for inputting a medical image picked up of a mucous surface of a living body; the feature value calculating section 31, which is feature value calculating means for calculating predetermined feature values of each pixel or each region in the medical image; the structure region extracting section 32, which is structure region extracting means for extracting a desired structural object from the picked-up medical image as a structure region; the basic shape matching section 33, which is basic shape matching means for matching each pixel or each region in the structure region with any of the plurality of predetermined basic shapes based on the feature values calculated by the feature value calculating means, and the structural object region dividing section 34, which is structural object region dividing means for dividing the structural object into regions according to the respective predetermined basic shapes based on results of matching by the basic shape matching means.

Figure 3:
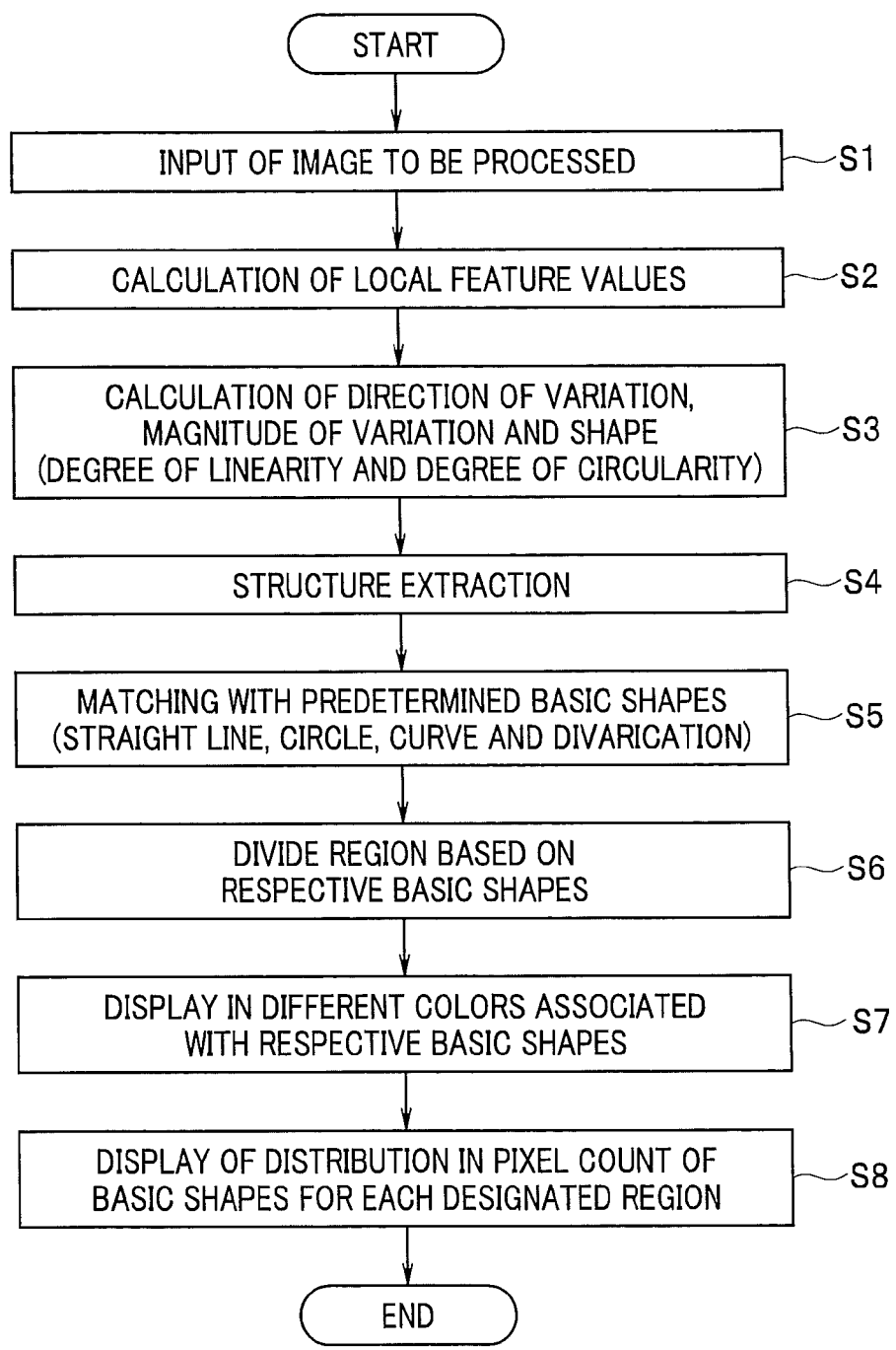
FIG. 3 is a flowchart illustrating a processing procedure according to the present embodiment.

Next, an operation of the present embodiment will be described with reference to a processing procedure according to the present embodiment, which is illustrated in FIG. 3. Upon a start of operation of the image processing apparatus 3, in first step S1, an image to be processed is inputted to the image processing apparatus 3 from the endoscopic observation apparatus 2 side via the image input section 21. The inputted image is stored in, for example, the image storing section 24.

FIG. 4(A) illustrates a part of the image inputted to the image processing apparatus 3. Also, FIG. 4(B) illustrates an enlargement of a partial image region of FIG. 4(A).

Figures 5, 6:
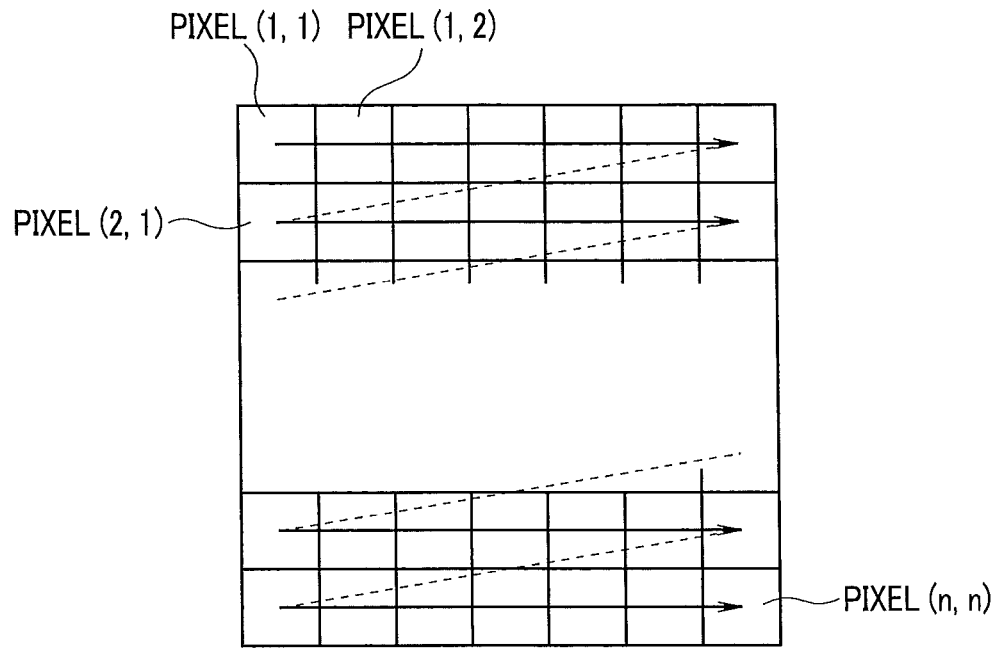
FIG. 5 is an operation illustration indicating a manner in which a pixel of interest is sequentially set in a medical image to perform, e.g., feature value calculation.
FIG. 6 is a diagram illustrating a manner in which feature values have been extracted for each pixel by the feature value calculating section.

In step S2, the feature value calculating section 31 in the CPU 22 calculates local feature values from the inputted image. In the present embodiment, for example, with all of pixels included in the image in FIG. 4(A) as processing targets, as illustrated in FIG. 5, all the pixels from the upper left pixel to the lower right pixel are sequentially set as a pixel of interest to calculate feature values.

For example, where a pixel that is the i-th in a horizontal direction and the j-th in a vertical direction is expressed as pixel (i, j) such that the upper left pixel is pixel (1, 1) and the pixel to the right of that pixel is pixel (1, 2), and the pixel below the upper left pixel (1, 1) is expressed as pixel (2, 1), scanning of all the pixels from pixel (1, 1) to pixel (n, n) is performed to calculate respective feature values as in FIG. 6. In FIG. 5, the pixel count of each of the horizontal direction and the vertical direction is n.

When feature values are calculated, each pixel may be set as a pixel of interest as described above or each region including a plurality of pixels, not each pixel, may be set.

When the feature value calculating section 31 in the present embodiment calculates local feature values, the feature value calculating section 31 calculates a first feature value relating to a direction of local variation (in a luminance value or a pixel value) of a pixel of interest, a second feature value relating to a magnitude of the local variation, and a third feature value relating to a shape based on the direction of the variation and the magnitude of the variation as illustrated in step S3.

More specifically, the feature value calculating section 31 in the CPU 22 calculates a Hessian matrix of two rows and two columns, which corresponds to second-order partial differential according to positions in the horizontal direction and the vertical direction, for a luminance value of each pixel to obtain eigenvalues $\lambda 1$ and $\lambda 2$ ($\lambda 1 \leq \lambda 2$) and eigenvectors e1 and e2 corresponding to the eigenvalues $\lambda 1$ and $\lambda 2$. The eigenvectors e1 and e2 correspond to a first feature value and the eigenvalues $\lambda 1$ and $\lambda 2$ correspond to a second feature value.

Also, the following arithmetic operation is performed on the second feature value to calculate a degree of linearity representing a degree of a pixel of interest having a characteristic of a linear shape, and a degree of circularity representing a degree of the pixel of interest having a characteristic of a circular shape.

Also, by means of feature value calculation, the feature value calculating section 31 calculates a degree of linearity $(\lambda 2 - \lambda 1)/\lambda 2$ by an arithmetic operation of $(\lambda 2 - \lambda 1)/\lambda 2$ and a degree of circularity $\lambda 1/\lambda 2$ by an arithmetic operation of $\lambda 1/\lambda 2$ as indicated in step S3.

FIG. 7A illustrates an example of shape feature values calculated for the case of the image in FIG. 4(B). FIG. 7A indicates that parts with a large degree of linearity (indicated by lines in FIG. 7A) and parts with a degree of circularity (indicated by circles in FIG. 7A) have been figured out.

A direction of gradient may be employed as the aforementioned first feature value. Also, a degree of gradient may be employed as the second feature value. Also, the third feature value may be a known shape index.

In step S4, which is illustrated in FIG. 3, the structure region extracting section 32 in the CPU 22 extracts a desired structural object from the image to be processed as a structure region.

In this case, means and method for extracting the structural object that is desired as a structure region are not limited to specific ones, and any of region dividing techniques such as simple binarization, snakes, level set and graph cut may be used.

After the aforementioned local feature values are calculated, a structural object may be extracted as a structure region based on the local feature values. A description is provided below in terms of a case where the local feature value calculation in step S2 is utilized.

The structure region extracting section 32 in the CPU 22 extracts, as a pixel forming a structure region that is a structural object (to be extracted), a pixel meeting any of the following four conditions:

The second feature value is no more than a certain threshold value T1high;

The second feature value is no less than a certain threshold value T1low (however, T1high>T1low);

The third feature value is no more than a certain threshold value T2high; and

The third feature value is no less than a certain threshold value T2low (however, T2high>T2low).

Such information on the threshold values T1high, T1low, T2high and T2low are stored in, for example, in the information storing section 25 in advance, and when the structure region extracting section 32 extracts a structural object as a structure region, the information stored in the information storing section 25 is used.

FIG. 7B illustrates an image in which a structure region extracted from the image in FIG. 4(A) has been extracted.

As indicated in step S5 in FIG. 3, the basic shape matching section 33 in the CPU 22 matches each pixel or each region in the structure region extracted as described above with any of a plurality of predetermined basic shapes based on the feature values calculated by the feature value calculating section 31.

In other words, which basic shape from among the plurality of predetermined basic shapes each pixel or each region in the extracted structure region corresponds to is determined to match the pixel or the region with the determined basic shape.

Furthermore, in the present embodiment, four types of basic shapes, i.e., a circle, a straight line, a curve and a divarication, which are minute-unit partial shapes included in a structural object in a mucous surface of a living body, are used as the plurality of predetermined basic shapes.

The four types of basic shapes, a circle, a straight line, a curve and a divarication, can be derived by determination in (a) to (d) below based on the aforementioned feature values for the degree of linearity and the degree of circularity.

The basic shape matching section 33 in the CPU 22 matches each pixel or each region in a structural object, which is a structure region, with any of the four basic shapes, i.e., a circle, a straight line, a curve and a divarication according to, for example, the feature values extracted in FIG. 6 as described below.

The basic shape matching section 33 in the CPU 22 performs matching with the basic shapes for each pixel or each region in a structural object, which is a structure region, so that the pixel or the region is matched with any of the respective basic shapes:
(a) a straight line if it is determined that the pixel or the region has a large degree of linearity and directions thereof concentrate on a certain direction;
(b) a curve if it is determined that the pixel or the region has a large degree of linearity and directions thereof concentrate on two different directions;
(c) a circle if it is determined that the pixel or the region has a large degree of circularity and directions thereof scatter; and
(d) a divarication if it is determined that the degree of linearity and the degree of circularity are almost equal to each other and directions from the pixel having a degree of linearity scatter in several directions.

For example, if it is determined that each pixel (or each region) in the aforementioned structural object, which is a structure region, has a large degree of linearity and directions thereof concentrate on a certain direction, it is determined that each pixel (or each region) has the basic shape of a straight line (or is formed by the basic shape of a straight line). A similar determination is made for other cases.

Although in the present embodiment, the matching is performed using the aforementioned four types of basic shapes, otherwise, basic shapes further classified according to characteristics, e.g., thickness, size and/or color may be applied.

In step S6 in FIG. 3, the structural object region dividing section 34 in the CPU 22 divides the structure region (which is a structural object) matched with the predetermined basic shapes in step S5 into regions based on the respective predetermined basic shapes.

As described above, the structural object extracted as a structure region enters a state in which the structural object can be expressed as one or more aggregates that have been divided into respective pixels or respective regions of the respective basic shapes. In other words, a structural object having a complicated shape can be evaluated, e.g., can be classified or categorized according to the basic shapes or basic shape patterns as an aggregate of components of a basic shape pattern, which is a pattern including a plurality of basic shapes, or an aggregate of a plurality of basic shape patterns.

If the structural object is divided into regions based on the respective basic shapes as in step S6, the image to be processed may be displayed with different colors further assigned to the respective basic shapes as illustrated in step S7.

FIG. 8(A) illustrates an image in which the image in FIGS. 4(A) and 7(B) is matched with the basic shapes as in step S6 and respective parts of the extracted structural object have been divided based on the respective basic shapes. FIG. 8(B) illustrates an image in which respective parts of the extracted structural object in the image in FIGS. 4(B) and 7(A) have been divided based on the respective basic shapes.

Where the image in FIG. 8 is displayed, different colors may be assigned to the respective basic shapes as in step S7 in FIG. 3 to provide display in false colors.

When display is provided in the false colors, even if a structural object having a complicated shape is matched with the basic shapes, distributions of the basic shapes can visually be understood easily.

Furthermore, for a designated region that is arbitrarily designated by a user such as a surgeon as in step S8, the CPU 22 may display distributions or a histogram in pixel counts of the respective basic shapes included in the designated region.

Consequently, quantitative reference data for performing, e.g., diagnosis can be provided to the surgeon. For example, when a region for which the surgeon makes diagnosis as to whether or not the region is a diseased part region is set as a first designated region and a normal region is set as a second designated region, quantitative distributions in pixel count of the basic shapes in each of the designated regions is displayed, and thus, the surgeon can use a result of comparison therebetween as reference data for making diagnosis.

The image processing in FIG. 3 ends with the processing in step S8.

In the present embodiment that operates as described above, since each pixel or each region included in an arbitrary structural object in an image to be processed is matched with any of the plurality of predetermined basic shapes, if the image to be processed has a complicated shape, an evaluation according to basic shape patterns can be made with a same processing procedure as described above without losing versatility.

Therefore, according to the present embodiment, even a medical image in which complicate patterns are formed can be matched with versatile patterns of a plurality of basic shapes, enabling provision of an image processing apparatus facilitating quantification. Steps S5 and S6 in FIG. 3 may be performed in combination.

Second Embodiment

Next, a second embodiment of the present invention will be described. The second embodiment of the present invention has a configuration resulting from the region setting section 35 indicated by the dotted lines in FIG. 2 or a region selecting section being provided to the first embodiment. The rest of configuration is similar to that of the first embodiment. The present embodiment enables a processing result with enhanced reliability to be obtained by performing additional processing to the basic processing in the first embodiment as described below.

As described above, the region setting section 35 selectively sets a first region including one or more pixels and a second region including at least one or more pixels in a peripheral portion of the first region. Then, when the first region and the second region have been set by the region setting section 35, the feature value calculating section 31 calculates feature values of the first region and the second region. Also, a basic shape matching section 33 matches the first region with predetermined basic shapes based on the feature values of the first region and the second region.

A processing procedure according to the present embodiment will be described with reference to the flowchart in FIG. 9. In the flowchart in FIG. 9, which indicates a processing procedure according to the present embodiment, processing in step S11 for setting a first region and a second region by means of the region setting section 35 is performed between steps S4 and S5 in the flowchart in FIG. 3.

A user such as a surgeon can perform an input of an instruction for selectively setting a first region and a second region via an input operation section 29. In this case, the region setting section 35 in a CPU 22 sets two positions or two regions designated by the instruction input as the first region and the second region.

Also, it is possible that the user performs an input of an instruction for selectively setting a first region via the input operation section 29 so that the region setting section 35 in the CPU 22 sets a position or a region designated by the instruction input as the first region and selectively sets a second region based on feature values of the set first region.

Also, it is possible that (all of pixels in) all of regions in an image to be processed are sequentially set as a first region and a second region is set in a peripheral portion of the first region at each position based on feature values of the first region.

Also, it is possible that a first region is sequentially set in a structure region in the image to be processed and a second region is set in a peripheral portion of the first region at each position based on feature values of the first region.

In the below example, a description will be provided focusing on a case where, for example, a first pixel in a first region is sequentially set in a structure region.

Also, in the present embodiment, a second region R2 in a peripheral portion of a first pixel in a first region, which will be described below, is set as a voting region.

The region setting section 35 sets a second region as described below based on feature values of a first region calculated by the feature value calculating section 31.

Figure 10:
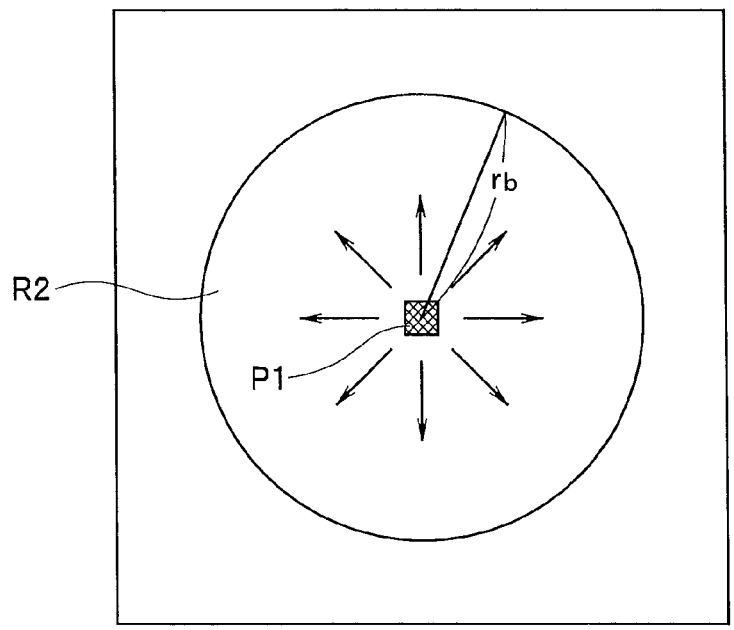
FIG. 10 is a diagram illustrating an example of a second region set in a peripheral portion of a first pixel forming a first region where the first pixel has a feature value with a large degree of circularity.

FIG. 10 illustrates an example of a second region R2 set where a first pixel P1 included in a first region is set (by a user) and the first pixel P1 has feature values indicating a large degree of circularity.

In the example illustrated in FIG. 10, where the first pixel P1 has feature values indicating a large degree of circularity, a second region R2 having a circular shape similar to that indicated by the feature values of the first pixel P1 is set in a periphery thereof.

The first pixel P1 has feature values exhibiting a large degree of circularity, and the region setting section 35 sets a second region R2 having a circular shape similar to a shape indicated by the degree of circularity is set in the periphery of the first pixel P1 based on the shape indicated by the feature values. A parameter that determines a region range of the second region R2 is a radius $r_b$, and a size of the radius $r_b$ is set to, for example, around 10-12 pixels. In other words, using a pixel position i in a horizontal direction and a pixel position j in a vertical direction, the second region R2 is determined by $i^2+j^2<r_b^2$.

Figure 11:
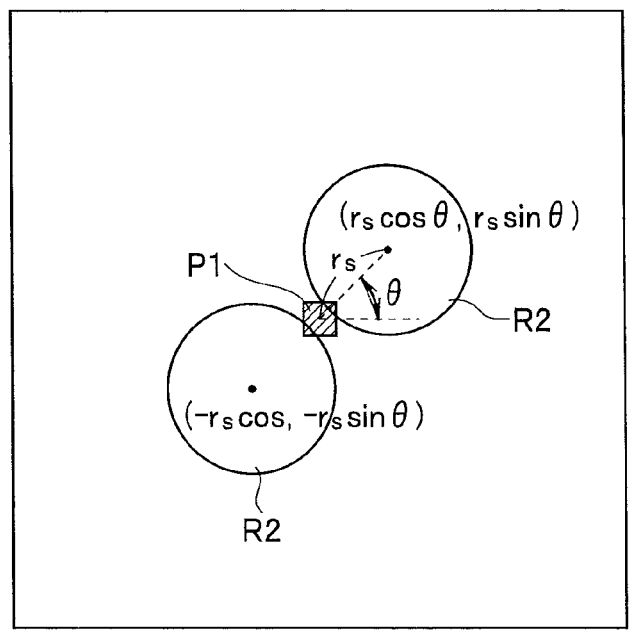
FIG. 11 is a diagram illustrating an example of a second region set in a peripheral portion of a first pixel forming a first region where the first pixel has a feature value with a large degree of linearity.

FIG. 11 illustrates an example of a second region R2 set where a first pixel P1 has feature values having a large degree of linearity, not circularity.

The first pixel P1 has feature values indicating a large degree of linearity, and the region setting section 35 sets a second region R2 having a shape close to a linear shape extending in directions in which variation in pixel value is the smallest (figure of eight in FIG. 11), as feature values for a degree of linearity, in a periphery of the first pixel P1 based on a shape indicated by the feature values. Parameters for determining a region range of the second region R2 in this case are: a second principal direction in which variation in pixel value is the smallest, the direction forming an angle θ (and θ+π) with the horizontal pixel direction; and a radius $r_s$. The radius $r_s$ is set as, for example, around five or six pixels. A direction orthogonal to the second principal direction is a first principal direction.

Also, the region range of the second region R2 expressed by θ and the radius $r_s$ is a range meeting either $(i-r_s \cos θ)^2+(i-r_s \cos θ)^2<r_s^2$ or $(i+r_s \cos θ)^2+(i+r_s \cos θ)^2<r_s^2$.

Figure 12:
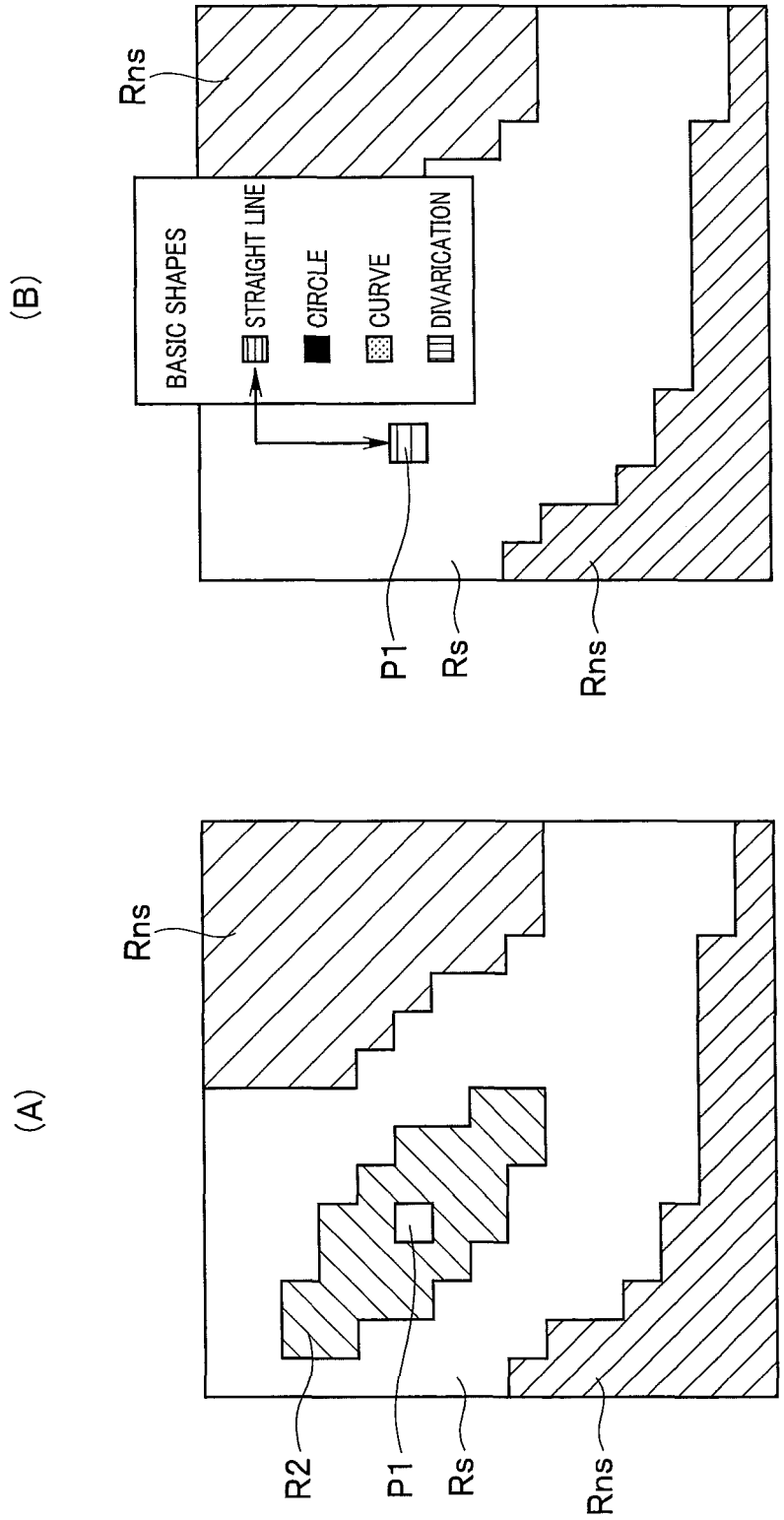
FIG. 12 includes diagrams illustrating an operation in which a second region is selectively set in a peripheral portion of a first pixel forming a first region and the first pixel is matched with any of basic shapes based on feature values of the second region.

Although FIG. 11 indicates an example in which the second region R2 is formed by two circular regions, the second region R2 may be formed by two flattened circles (an example thereof is indicated in FIG. 12, for example).

Figure 9:
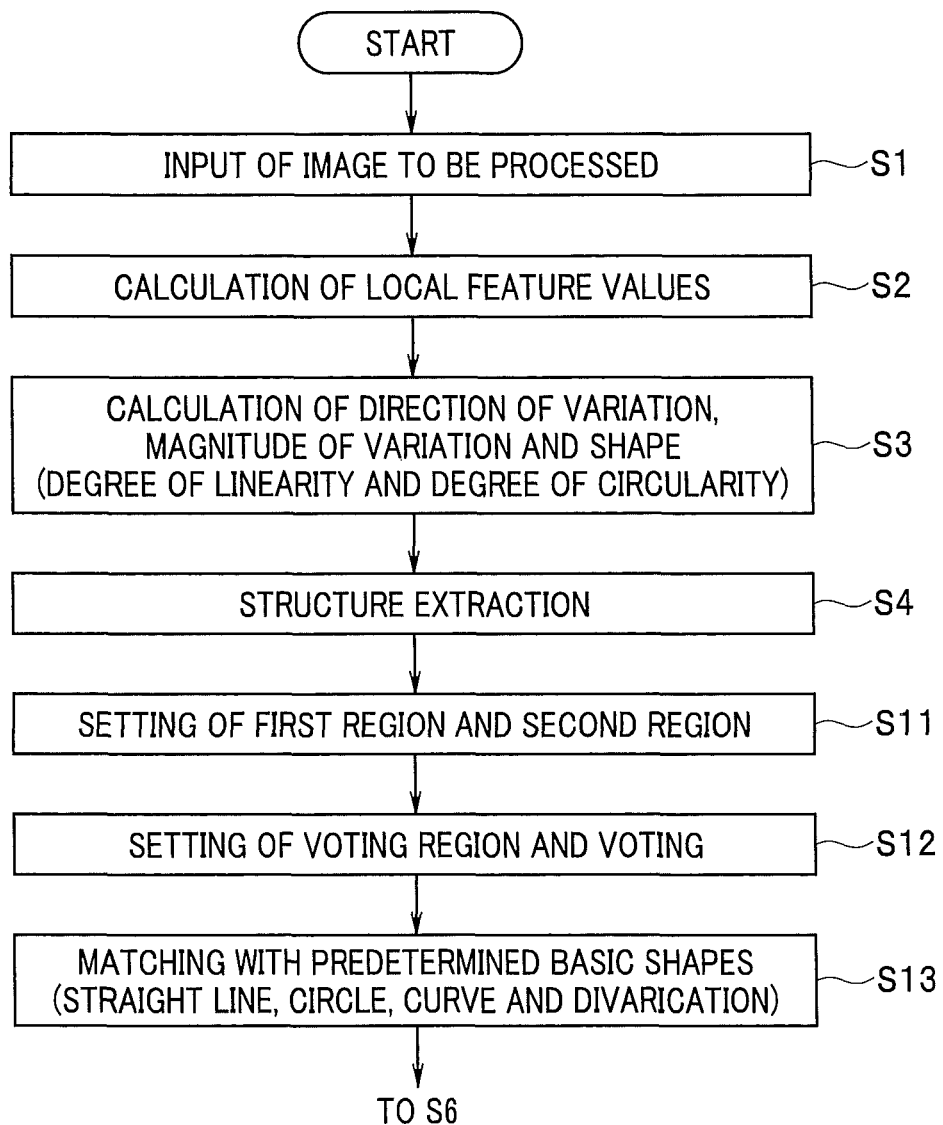
FIG. 9 is a flowchart illustrating a processing procedure according to a second embodiment of the present invention.

After the second region R2 is set as described above, voting is performed with the second region including the first region R1 set as a voting range as indicated in step S12 in FIG. 9.

Voting processing for storing feature values of the first pixel P1 in each memory cell (which forms a voting information storing section) provided corresponding to each pixel in the second region R2 is performed for, for example, all of first pixels forming the structure region.

Each memory cell enters in a state in which the memory cell waits for information on a result of the voting for a two-dimensional distribution of the feature values of the first pixel P1. Also, information in each memory cell can be regarded as having feature values of the second region in the peripheral portion.

In next step S13, based on the voted feature values, processing for matching with predetermined basic shapes, which corresponds to step S5 in FIG. 3, is performed.

In the case of FIG. 3, in step S5, processing for matching with the predetermined basic shapes is performed based on the feature values of the individual first pixels P1.

In contrast, in step S13 in the present embodiment, feature values of a first pixel are calculated, and processing for matching with predetermined basic shapes is performed based on feature values that are results of voting for a two-dimensional distribution in a peripheral portion of the first pixel.

More specifically, the basic shape matching section 33 in the CPU 22 matches each pixel or each region in a structural object, which is a structure region, with any of the basic shapes so that the pixel or the region is matched with any of the respective basic shapes:

(a) a straight line if it is determined that the voting has been performed so as to provide a large degree of linearity and directions of the pixel or the region concentrate on a certain direction;

(b) a curve if it is determined that the voting has been performed so as to provide a large degree of linearity and directions of the pixel or the region concentrate on two different directions;

(c) a circle if it is determined that the voting has been performed so as to provide a large degree of circularity and directions of the pixel or the region scatter; and (d) a divarication if it is determined that the voting has been performed so as to provide a degree of linearity and a degree of circularity that are almost equal to each other, and directions from the pixel having a degree of linearity scatter in several directions.

FIG. 12 includes operation illustrations in this case. FIG. 12(A) indicates a state in which a second region R2 has been set in a periphery of a first pixel P1, which is a pixel in a first region, by the region setting section 35. The image in FIG. 12(A) indicates that a structure region Rs has been extracted by the above-described structure region extracting section 32 and Rns denotes a non-structure region, which is a structure region not falling under the structure region Rs.

In this case, the pixel P1 in the first region is matched with any of basic shapes based on extracted feature values of the first region and the second region R2.

In the second embodiment, as a result of the second region R2 being set in a voting range, the first pixel P1 in the first region has feature values reflecting the feature values of the second region R2, and matching with basic shapes is performed based on the feature values.

FIG. 12(B) indicates that the pixel P1 in the first region has been matched with one of the basic shapes, and the example in FIG. 12(B) indicates that it is determined that the first pixel P1 has the basic shape of a straight line because the first pixel P1 is matched with the basic shape of a straight line.

Figure 13:
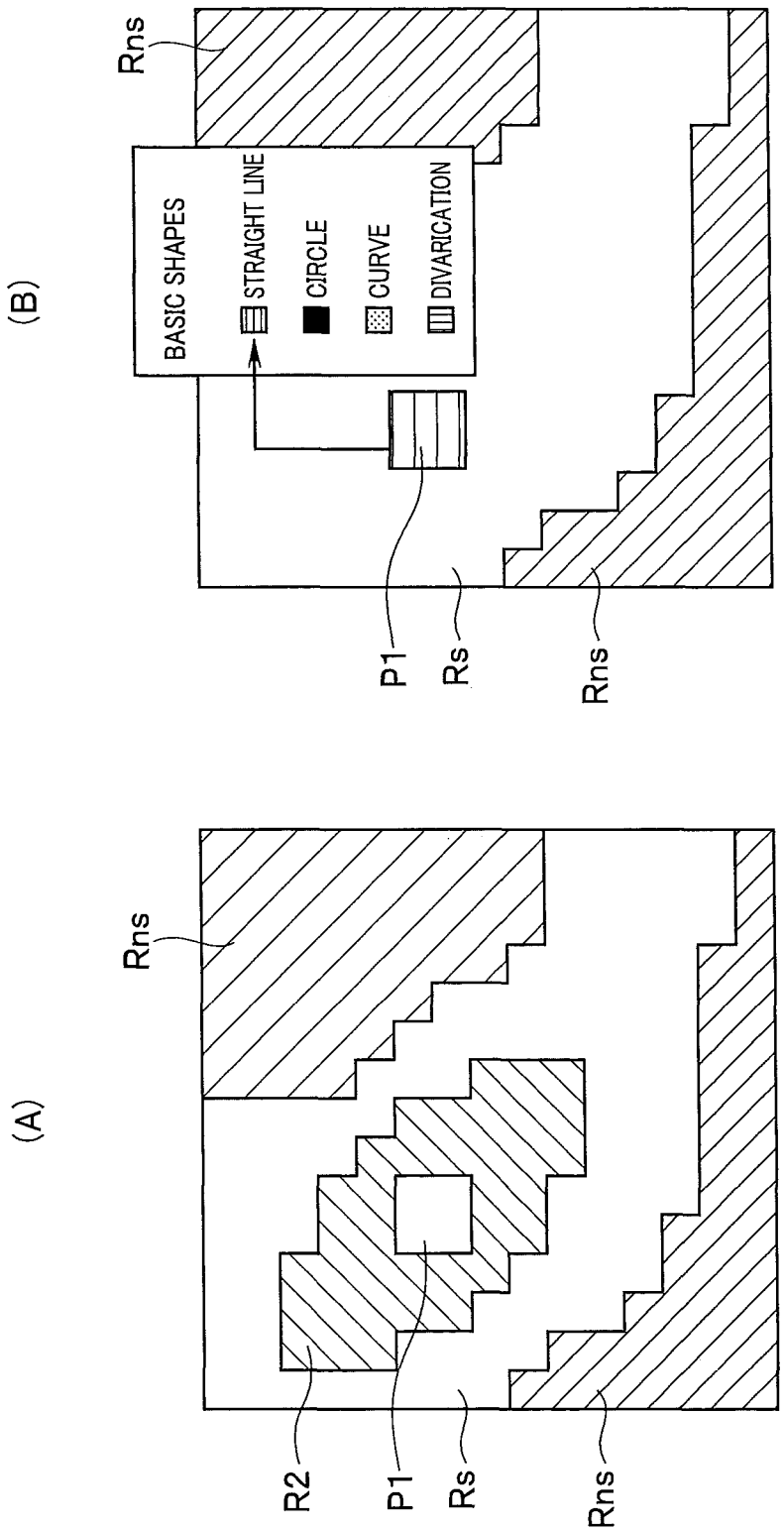
FIG. 13 includes diagrams illustrating an operation in which a first region is selectively set instead of the first pixel in FIG. 12 and the first region is matched with any of basic shapes based on feature values of the first region.

Although FIGS. 12(A) and 12(B) indicate a case where a second region R2 is set in a periphery of a pixel P1 in a first region, as illustrated in FIGS. 13(A) and 13(B), a second region R2 may also be set in a periphery of a first region R1. FIG. 13 is different from FIG. 12 only in that the first pixel P1 in FIG. 12 is changed to the first region R1, and thus a description thereof will be omitted. Also, the second region R2 is not limited to a case where the second region R2 includes a plurality of pixels, and may include one pixel.

After step S13 in FIG. 9, as in the case of FIG. 3, the processing in step S6 is performed and the processing in step S6 onwards is similar to that in the case of FIG. 3.

When matching with the basic shapes is performed in such a manner as described above, the matching with the basic shapes can be performed in consideration of feature values of pixels in the periphery of the pixel P1 in the first region compared to a case where the matching with the basic shapes is performed based only on the pixel P1. Thus, where the pixel values are affected by noise, matching with the basic shape can be performed with a reduced effect of noise.

Besides, as in the first embodiment, the present embodiment enables provision of an image processing apparatus that even in the case of a medical image having a complicated pattern, enables matching with a plurality of versatile basic shape patterns, facilitating quantification.

In the above description, image processing in which a voting range is set to perform voting functions effectively in the case where feature values of the first pixel P1 or the first region R1 include those for the basic shape of a divarication (matching with the basic shape of a divarication). Reasons therefor will be described below with reference to FIG. 14.

Where the first pixel P1 (or a region in a vicinity thereof) has feature values for a divarication, as illustrated in FIG. 14, the first pixel P1 (or the region in the vicinity thereof) can be considered as being generated in a region R3 where a circular second region R2a and an eight-figure second region R2b overlap between a pixel P1a having feature values for a degree of circularity and a pixel P1b having feature values for a degree of linearity.

In such case, a voting range for performing voting according to the feature values for the degree of circularity and the feature values for the degree of linearity is set enables extraction of a pixel or the region R3 having a divarication, which has the feature values for the both.

Besides the case of the second region R2 such as illustrated in FIGS. 10 and 11, a second region R2 may be set as illustrated in FIG. 15.

For example, if a first image P1 in FIG. 15(A) has feature values with, for example, a large degree of circularity, as illustrated in FIG. 15(B), a second region R2 having a shape close to a circular shape is set in a periphery of the first pixel P1 (an example in which a second region R2 with a smaller pixel size compared to the case of FIG. 10 is set is indicated).

Also, if the first pixel P1 in FIG. 15(A) has feature values for a large degree of linearity, as illustrated in FIG. 15(C), a second region R2 having a belt-like shape extending in a direction in which variation in degree of linearity is small is set in a peripheral section (periphery) of the first pixel P1.

Also, if a second region R2 is selectively set, the second region R2 is selected based on positions or feature values of candidate regions which are candidates for the second region.

Figure 16:
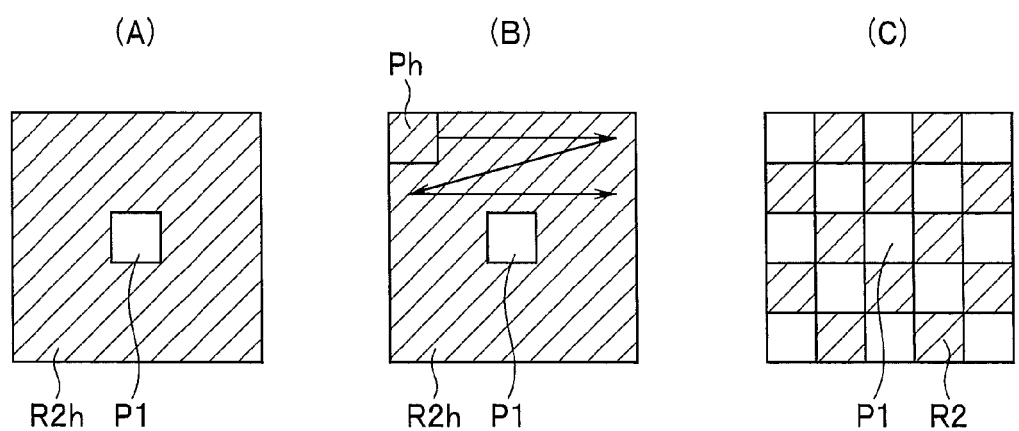
FIG. 16 includes diagrams illustrating an operation in which a second region is set from candidate regions based on feature values of the candidate regions.

FIG. 16 illustrates that a candidate region R2h is set in a periphery of a first pixel P1 and a second region R2 is selectively set according to feature values of each candidate pixel Ph in the candidate region R2h.

FIG. 16(A) indicates a candidate region R2h tentatively set in the periphery of the first pixel P1, and as illustrated in FIG. 16(B), each candidate pixel Ph in the candidate region R2h is scanned and at that time, whether or not each candidate pixel Ph is selected as (a second pixel in) a second region R2 is determined based on feature values of each candidate pixel Ph. Then, as a result of the processing in FIG. 16(B) being performed over the entire candidate region R2h, a second region R2 is determined, for example, as illustrated in FIG. 16(C).

In such case, for example, matching of the first pixel P1 with any of basic shapes can be performed in such a manner that the candidate region R2h is narrowed down so as to exclude a region not suitable for the second region R2.

Although FIG. 16 indicates a case where a second region R2 is set based on feature values of each pixel in a candidate region R2h, a second region R2 may be set based on a position of each pixel in a candidate region R2h. For example, a pixel close to the first pixel P1 may be set so as to be included in a second region R2.

Also, in FIG. 16, it is possible that a first region R1 is set instead of the first pixel P1 and a candidate region R2h is set in a periphery thereof, and a second region R2 is set as in such a manner as in the above-described case.

Figure 17:
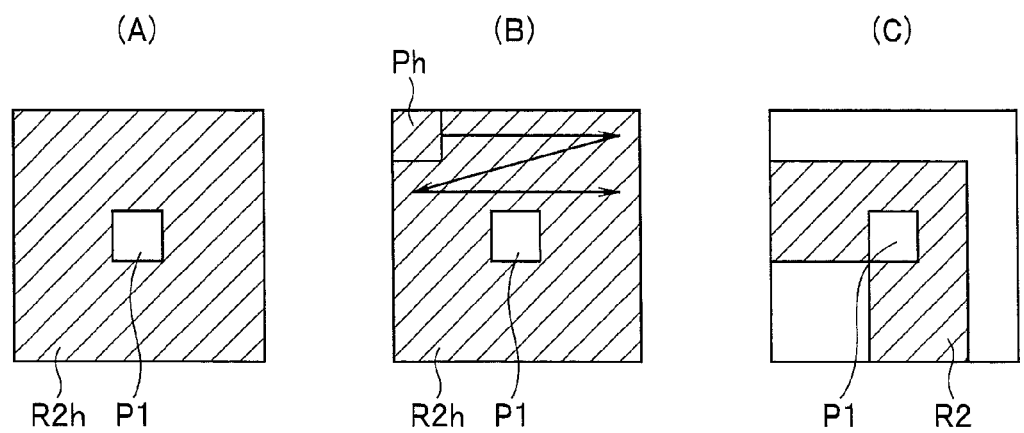
FIG. 17 includes diagrams illustrating an operation in which a second region is set from candidate regions based on feature values of the candidate regions and a feature value of a first pixel.

Also, although FIG. 16 indicates a case where if a candidate region R2h is selectively set, a second region R2 is set based on a position or feature values of the candidate region, a second region R2 may be selectively set based on a position or feature values of a candidate region and a position or feature values of a first pixel P1 or a first region R1. FIG. 17 illustrates an example of this case.

As in FIG. 16(A), FIG. 17(A) illustrates a candidate region R2h tentatively set in a periphery of a first pixel P1. In FIG. 17(B), each candidate pixel Ph in the candidate region R2h is scanned and at that time whether or not each candidate pixel Ph is set as (a second pixel in) a second region R2 is determined based on feature values of each candidate pixel Ph and feature values of the first pixel P1. Then, as a result of the processing in FIG. 17(B) being performed over the entire candidate region R2h, a second region R2 is determined, for example, as illustrated in FIG. 17(C).

In such case, for example, a region not related to the first pixel P1 can be excluded from the candidate region R2h to narrow the candidate region R2h down to the second region R2 relating to the first pixel P1, enabling the first pixel P1 to be more reliably matched with any of basic shapes.

Although FIG. 17 indicates a case where a second region R2 is set based on feature values of each pixel in the candidate region R2h and the first pixel P1 as described with reference to FIG. 16, a second region R2 may be set based on a position of each pixel in the candidate region R2h and a position or feature values of the first pixel P1.

Also, a second region R2 may be set based on the feature values of each pixel in the candidate region R2h and the position of the first pixel P1.

Also, in FIG. 17, it is possible that a first region R1 is set instead of the first pixel P1, a candidate region R2h is set in a periphery thereof, and a second region R2 is set in such a manner as in the above-described case.

Figure 18:
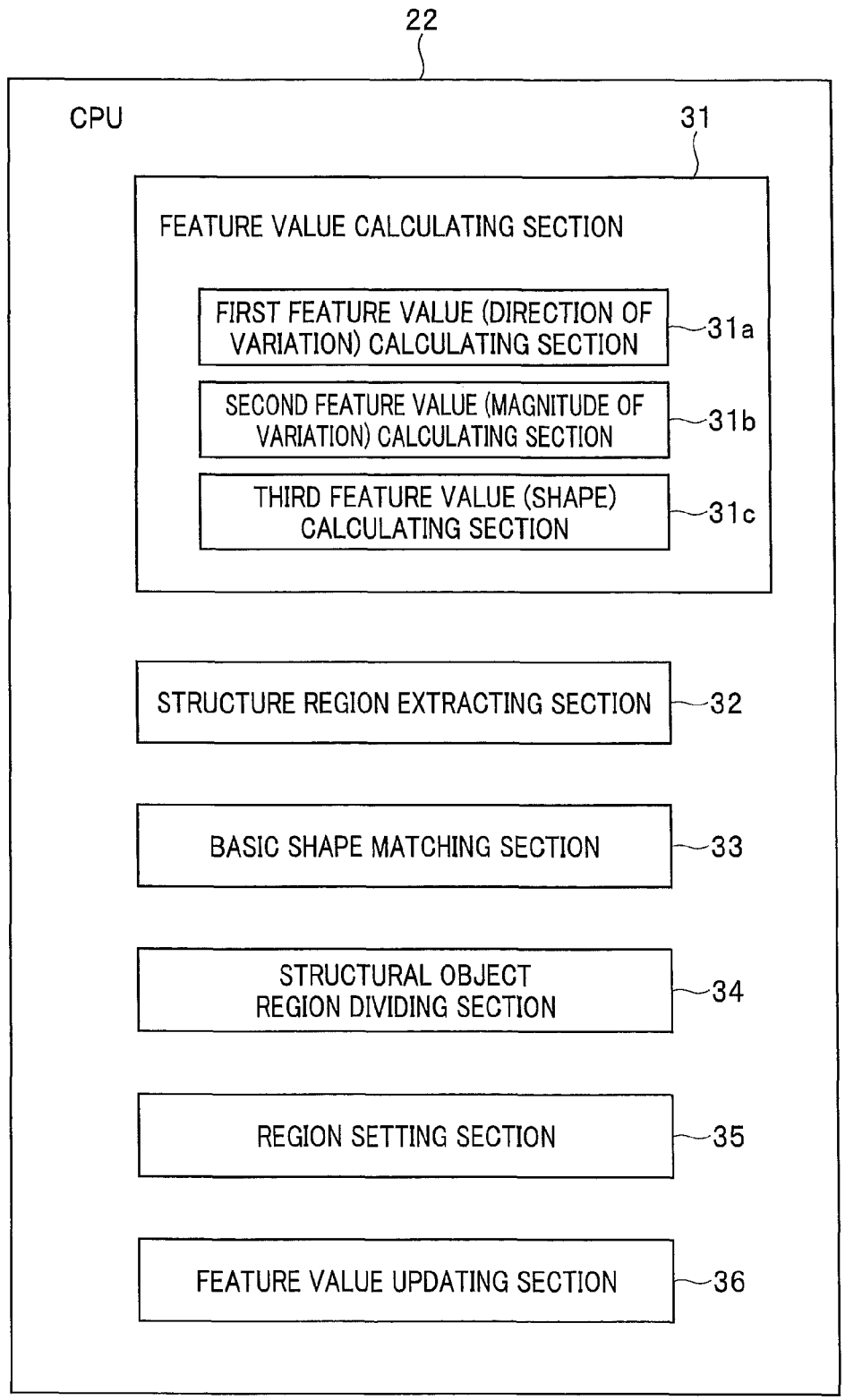
FIG. 18 is a block diagram illustrating a configuration of processing functions in a CPU according to a modification of the second embodiment.

As in a modification, which is illustrated in FIG. 18, a feature value updating section 36, which is feature value updating means, may be provided in a CPU 22. The feature value updating section 36 varies feature values of at least one of a first region R1 and a second region R2 based on the feature values of the first region R1 or the feature values of the second region R2 to update the feature values.

Also, the region setting section 35 selectively sets a second region based on a result of the update by the feature value updating section 36.

Figure 19:
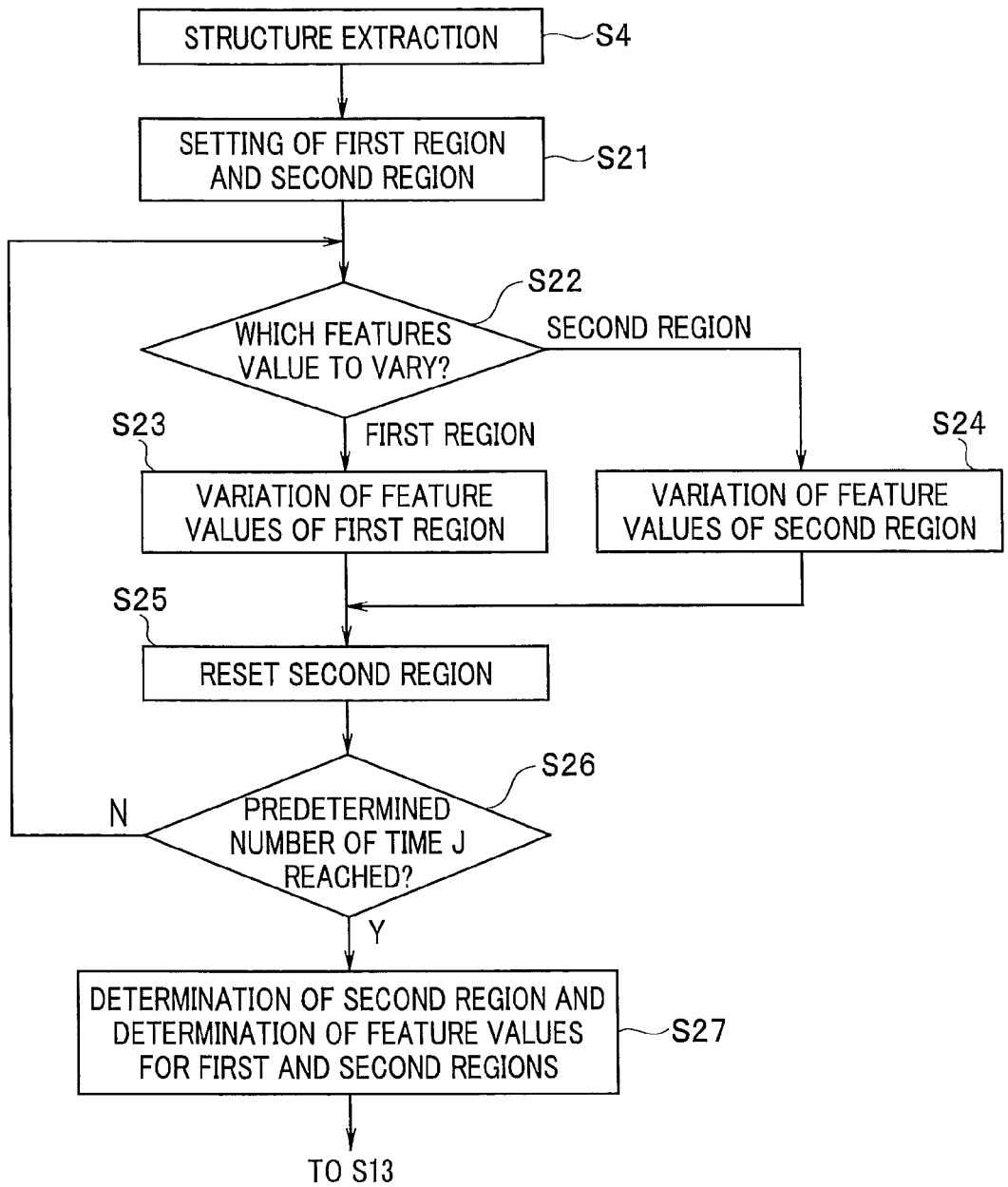
FIG. 19 is a flowchart illustrating an example of a processing procedure for varying a feature value of at least one of a first region and a second region to selectively set a second region.

FIG. 19 illustrates an example of a processing procedure in this case. In FIG. 19, a first region R1 and a second region R2 are set as indicated in step S21 subsequent to step S4 in FIG. 9.

The setting of a first region R1 and a second region R2 in step S21 can be made by any of the above-described methods according to the second embodiment. However, in the present modification, the setting in step S21 is a tentative setting as can be seen from the below description.

FIG. 20(A) illustrates examples of the first region R1 and the second region R2 set in step S21.

A user performs an input of an instruction regarding which feature values to vary (update), from among feature values of the first region R1 and feature values of the second region R2, via an input operation section 29 to a feature value updating section 36.

As indicated in step S22, the feature value updating section 36 determines which feature values to vary according to the input of the instruction. Also, it is possible that at the time of, e.g., initial settings, which feature values to vary is determined in a CPU 22 in advance by means of, e.g., a program, and the feature value updating section 36 automatically varies the feature values according to the settings. Also, the feature values may be alternately varied.

If a determination (setting) is made so as to vary the feature values of the first region R1, as indicated in step S23, the feature values of the first region R1 are varied, and the procedure proceeds to processing in step S25.

On the other hand, if a determination (setting) is made so as to vary the feature values of the second region R2, as indicated in step S24, the feature values of the second region R2 are varied and the procedure proceeds processing in step S25.

Here, when the feature values of the first region R1 or the feature values of the second region R2 are varied, the feature values are varied within a threshold value range corresponding to a noise level of each pixel included in the first region R1 or the second region R2.

In step S25, the region setting section 35 resets a second region R2 based on the feature values of the first region R1 and the feature values of the second region R2, and the procedure proceeds to step S26.

In step S26, the feature value updating section 36 determines whether or not processing for varying the feature values in a set number of time J (J is a natural number) has been performed, and if the feature value updating section 36 determines that the set number of times J has not been reached, the procedure returns to the processing in step S22. Then, the processing in steps S22 to S26 is repeated.

On the other hand, if it is determined that the set number of times J has been reached, the procedure proceeds to processing in step S27, and the region setting section 35 determines a second region R2 and the feature value updating section 36 determines respective feature values of the first region R1 and the second region R2.

If the above-described feature values have been varied in the set number of times J, the region setting section 35 monitors a relative amount of variation of the respective reset second region R2, and determines a second region R2 with a smallest amount of variation of the second region R2 relative to the variation of the feature values as a second region R2 in step S26.

FIG. 20(B) illustrates the first region R1 and the second region R2 determined in step S26.

After the processing in step S26, in next step S13, matching with basic shapes is performed. The processing in step S13 onwards is similar to that in FIG. 9.

As a result of the processing such as indicated in FIG. 19 being performed, for each pixel, feature values that are easily affected by noise and a second region R2 set based on the feature values can be updated to feature values and a second region R2 with the effect of noise mitigated.

Besides, effects substantially similar to those of the second embodiment can be provided.

Each of embodiments formed by, e.g., changing a combination in the above-described embodiments and the like also belongs to the present invention.

What is claimed is:

1. An image processing apparatus comprising:
   an image input section via which a medical image picked up of a mucous surface of a living body, the medical image including a plurality of pixels, is inputted;
   a region setting section that sets a first region including one or more pixels in the medical image;
   a feature value calculating section that calculates a degree of linearity representing a degree of the first region having a characteristic of a linear shape and a degree of circularity representing a degree of the first region having a characteristic of a circular shape based on a luminance value of the first region set by the region setting section and a luminance value of a region in a periphery of the first region; and
   the region setting section further setting a second region which includes one or more pixels in a peripheral portion of the first region based on the degree of linearity and the degree of circularity calculated by the feature value calculating section,
   the feature value calculating section further calculating a degree of linearity representing a degree of the second region having a characteristic of a linear shape and a degree of circularity representing a degree of the second region having a characteristic of a circular shape based on the luminance value of the second region,
   a basic shape matching section that matches the first region with a predetermined shape based on distributions of the degree of linearity and the degree of circularity of the first region and the degree of linearity and the degree of circularity of the second region calculated by the feature value calculating section.

2. The image processing apparatus according to claim 1, further comprising
   a structure region extracting section that extracts a desired structural object from the medical image as a structure region,
   wherein the region setting section sets the first region in the structure region extracted by the structure region extracting section.

3. The image processing apparatus according to claim 1,
wherein the feature value calculating section further calculates a feature value relating to a direction of local variation in luminance value of the first region; and
wherein the basic shape matching section matches the first region with the predetermined shape based on distributions of the degree of linearity and degree of circularity of the first region and the degree of linearity and degree of second circularity of the second region, and the feature value relating to the direction of local variation in luminance value of the first region.

* * * * *